United States Patent [19]

Heldebrant et al.

[11] Patent Number: 4,769,241

[45] Date of Patent: Sep. 6, 1988

[54] APPARATUS AND PROCESS FOR OXYGENATION OF LIQUID STATE DISSOLVED OXYGEN-CARRYING FORMULATION

[75] Inventors: Charles M. Heldebrant, Arcadia; Kim C. Crowe, Northridge; George R. Groveman, Clairmont; Charles H. Davis, Jr., Mission Viejo, all of Calif.

[73] Assignee: Alpha Therapeutic Corporation, Los Angeles, Calif.

[21] Appl. No.: 910,521

[22] Filed: Sep. 23, 1986

[51] Int. Cl.$^4$ .............. A61K 33/04; A61K 33/06; A61K 31/13; A61K 31/03

[52] U.S. Cl. ...................... 424/161; 424/127; 514/672; 514/753; 514/832; 514/833

[58] Field of Search .............. 424/127, 161; 514/753, 514/672, 832, 833

[56] References Cited

U.S. PATENT DOCUMENTS

| | | | |
|---|---|---|---|
| 1,808,854 | 6/1931 | Malone | 261/70 |
| 1,943,903 | 1/1934 | Treanor | 261/75 |
| 2,241,018 | 5/1941 | Lloyd | 261/75 |
| 2,693,802 | 11/1954 | Osborn | 422/45 |
| 2,702,035 | 2/1955 | Gibbon | 422/45 |
| 2,827,901 | 3/1958 | Jones | 128/214 |
| 3,015,331 | 1/1962 | Warrick | 128/214 |
| 3,183,908 | 5/1965 | Collins | 422/45 |
| 3,212,499 | 10/1965 | Koreski | 128/214 |
| 3,276,589 | 10/1966 | Jankay | 210/175 |
| 3,406,531 | 10/1968 | Swenson et al. | 424/127 |
| 3,515,640 | 6/1970 | Rudlin | 195/1.8 |
| 3,536,451 | 10/1970 | Ludwin | 23/258.5 |
| 3,639,084 | 2/1972 | Goldhaber | 422/44 |
| 3,733,776 | 5/1973 | Li et al. | 55/16 |
| 3,832,139 | 8/1974 | Runck et al. | 23/253 |
| 3,942,527 | 3/1976 | Li et al. | 128/214 |
| 3,962,439 | 6/1976 | Yokoyama et al. | 514/832 |
| 4,183,962 | 1/1980 | Asher | 424/366 |
| 4,252,827 | 2/1981 | Yokoyama et al. | 514/776 |
| 4,464,337 | 8/1984 | Zelman | 422/41 |

*Primary Examiner*—Albert T. Meyers
*Assistant Examiner*—John M. Kilcoyne
*Attorney, Agent, or Firm*—Christie, Parker & Hale

[57] ABSTRACT

Perfluorocarbon emulsion formulations are oxygenated prior to use by means of a portable oxygenation system. The blood substitute is in a closed container or bag. An oxygen-containing gas is introduced into the bag from a separate container. The bag is continuously agitated for a sufficient time to increase the pO$_2$ of the perfluorocarbon emulsion formulations to a desired pressure, e.g., to at least 600 mmHg. In one embodiment, the system used for oxygenation of the perfluorocarbon emulsion formulations comprises a small tank for gas having an inlet port and an outlet port fitted with shut-off valves. The outlet port is adapted to be connected to a filter which, in turn, is adapted to be connected to the inlet port of a three-way valve. The primary outlet of the three-way valve is adapted to mount a hypodermic needle which is adapted to be pushed through a rubber septum in a port of the bag to communicate with the interior of the bag. The tank is adapted to be filled with oxygen-containing gas, such as carbogen, from a main gas source under pressure. The tank, filter, three-way valve and needle arrangement are connected in series, and the oxygen-containing gas is permitted to flow from the tank into the bag holding the emulsion formulation. After the gas is introduced into the bag, the three-way valve is closed to prevent leakage of the gas from the container. The container is then agitated to oxygenate the emulsion formulation.

11 Claims, 4 Drawing Sheets

APPARATUS AND PROCESS FOR OXYGENATION OF LIQUID STATE DISSOLVED OXYGEN-CARRYING FORMULATION

FIELD OF THE INVENTION

This invention relates to a method and apparatus for the oxygenation of perfluorocarbon emulsion formulations.

BACKGROUND OF THE INVENTION

Blood is a highly complex liquid with many components and a variety of functions, the most important of which include transport of oxygen and metabolic substances to tissues, removal of carbon dioxide and metabolic products, and maintenance of the concentration of ions and other solutes in the extracellular fluids. Ischemia results from a lack of blood flow to the affected tissues. Such tissues show reduced function, and may be permanently damaged, or may even die. Ischemic modifiers, such as perfluorocarbon chemical emulsions, function to provide oxygen to tissues made ischemic by lack of blood flow. In so doing, they promote near normal or enhanced tissue function, hence they act as ischemic modifiers. In 1966, Leland C. Clark, Jr. of the University of Cincinnati College of Medicine, demonstrated the high oxygen solubility of perfluorochemicals. Normal saline or blood plasma dissolves about 3 volume percent oxygen and whole blood about 20 volume percent oxygen. In contrast, perfluorochemicals dissolve about 40 volume percent or more of oxygen. In addition, perfluorocarbon compounds dissolve even more carbon dioxide.

Since 1966, a number of investigators have worked on the development of perfluorocarbon chemical formulations as blood substitutes and a ischemic modifiers. The perfluorocarbon chemical formulations normally comprise an emulsion of perfluorocarbon chemicals in an aqueous media. For biological purposes, these emulsions may also contain electrolytes, such as sodium chloride, potassium chloride, magnesium chloride, calcium chloride, sodium bicarbonate and metabolites, such as glucose. A discussion of perfluorocarbon chemical emulsions is set forth in PERFLUOROCHEMICAL BLOOD SUBSTITUTES (FC-43 EMULSION) (FLUOSOL ®-DA, 20% and 35%) (FLUOSOL ® is a registered trademark of Alpha Therapeutic Corporation, Los Angeles, Calif.) FOR PRECLINICAL STUDIES AS A CANDIDATE FOR ERYTHROCYTE SUBSTITUTION BY R. NAITO AND K. YOKOYAMA; Technical Information Ser. No. 5; June 30, 1978, revised July 1, 1981; The Green Cross Corporation, Osaka, Japan and PERFLUOROCHEMICAL BLOOD SUBSTITUTES (FC-43 EMULSION) (FLUOSOL ®-DA, 20%, 35%) AS AN OXYGEN-CARRYING COLLOIDAL BLOOD SUBSTITUTE; Technical Information Ser. No. 7; July 30, 1981; The Green Cross Corporation, Osaka, Japan. The disclosure of both these publications is incorporated herein by reference.

Perfluorochemical emulsion formulations are normally supplied in plastic bags which are gas-permeable. Accordingly, perfluorochemical emulsion formulations are not oxygenated at the time of packaging, since the oxygen in the bag can diffuse out through the plastic bag and the nitrogen in the air can diffuse into the plastic bag to obtain an equilibrium gas mixture inside and outside the bag. In practice, the perfluorochemical emulsion formulation is oxygenated at a time just prior to use.

Previous methods used for oxygenation of perfluorocarbon emulsion formulations include bubbling an oxygen containing gas, such as a mixture of 95% oxygen and 5% carbon dioxide by volume (medical oxygen commonly called carbogen), through the perfluorocarbon emulsion while it is in its plastic bag. Another method is to remove a portion of the perfluorocarbon emulsion from the bag, place it into another container, bubble the oxygen containing gas through it and then return it to the plastic bag. Finally, perfluorocarbon emulsions have been oxygenated by passing them through an oxygenation device such as a membrane oxygenator. Although the above described prior art methods are all effective in oxygenating blood substitutes to an adequate partial pressure of oxygen, ($pO_2$), they can compromise the sterility or integrity of the product in one manner or another or are inconvenient to use in a hospital setting.

A simple and inexpensive method and apparatus is needed for enabling a medical practitioner to oxygenate perfluorochemical emulsion formulations in the bag so that the final product is sterile and attains a predictable $pO_2$ upon oxygenation.

SUMMARY OF THE INVENTION

The present invention is directed to a method and system for oxygenating a perfluorocarbon emulsion formulation. A preferred embodiment of such a method comprises the steps of placing a perfluorocarbon emulsion formulation in a closed container such as a plastic bag. An oxygen-containing gas is then introduced into the bag from a separate container and the bag is agitated. Such agitation is conducted for a time sufficient to dissolve oxygen in the perfluorocarbon emulsion formulation so that the oxygen in the oxygen-containing gas above the emulsion formulation approaches equilibrium with the oxygen dissolved in the perfluorocarbon emulsion formulation.

In a preferred embodiment of the present invention, a sufficient amount of the oxygen containing gas is introduced into the bag so that the partial pressure of the oxygen ($pO_2$) in the emulsion formulation at the completion of oxygenation is at least about 600 mmHg. More preferably, a sufficient amount of oxygen containing gas is introduced so that the $pO_2$ in the emulsion formulation at the completion of oxidation is at least about 720 mmHg.

One embodiment of a system used in accordance with practice of this invention for oxygenating the perfluorocarbon emulsion formulation includes a sealed flexible and pliable bag for containing the emulsion formulation which has a sealed multi-purpose port at one end. A three-way valve is provided that has one inlet and at least one outlet adapted to be connected to the sealed port of the bag for communication with the interior of the bag. A filter is provided which has an inlet and an outlet which is adapted to be connected to the inlet of the three-way valve. An oxygen gas reservoir assembly, including a gas reservoir of known volume, is provided with at least one port adapted to be connected to the inlet of the filter.

Preferably, the outlet of the three-way valve adapted to be connected to the sealed port of the container, includes a fitting configured to receive the female adapter of a standard hypodermic needle so that the needle can be connected to the three-way valve and inserted through the sealed port of the container. The needle can be used to transport the oxygen containing gas into the container and can also be utilized as a conduit for the introduction of other materials into the container or for sampling the contents of the container.

BRIEF DESCRIPTION OF THE DRAWINGS

These and other features, aspects and advantages of the present invention will be more fully understood when considered with respect to the following detailed description, appended claims, and accompanying drawings, wherein:

DETAILED DESCRIPTION OF THE INVENTION

Figure 1:
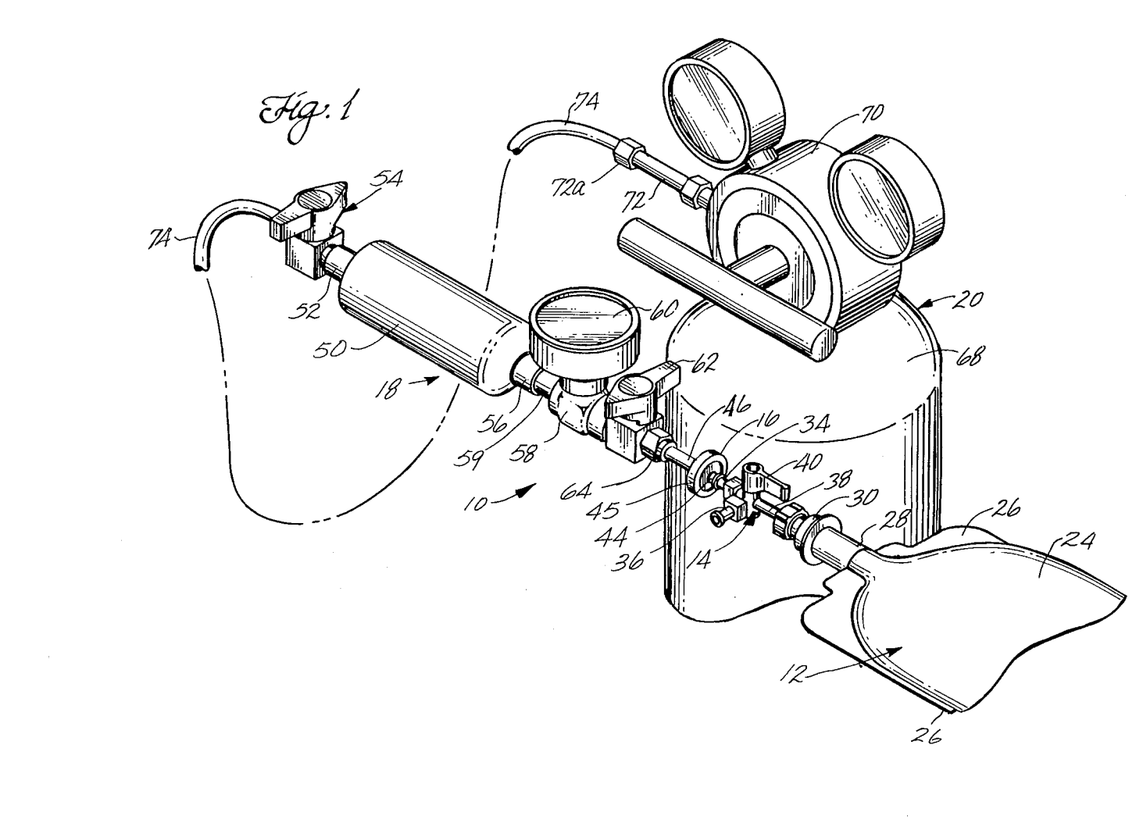
FIG. 1 is a perspective fragmentary view of one embodiment of an oxygenation system provided in accordance with practice of principles of the present invention.

Referring to FIG. 1, a preferred embodiment of a perfluorocarbon emulsion formulation oxygenating system 10 provided in accordance with practice of principles of the present invention is illustrated. The system 10 comprises a perfluorocarbon emulsion formulation containment bag or container 12, a three-way valve 14, a filter 16, an oxygen-containing gas reservoir assembly 18 and an oxygen-containing gas supply assembly 20.

The perfluorocarbon emulsion formulation containment bag 12 can be a conventional plastic containment bag used in the medical field, such as for blood, plasma, saline solution, glucose solution, dextrose solution and the like. The bag has an enlarged containment portion 24 sealed at the edges 26. The bag is fabricated with a neck portion 28 which has a multi-purpose port 30 sealed or plugged by means of a rubber septum (not shown) for receiving a hypodermic needle. Such containment bags come in a variety of standard sizes with capacities of from about 500 milliliters (mL) to about 1,000 mL of fluid. The bags are made of flexible pliable plastic which is puncture and tear resistant. The bags are impermeable to most liquids, including water, but are permeable to gasses such as nitrogen ($N_2$) and oxygen ($O_2$). Such a bag is a MEDIDEX brand bag provided by Naniwa Rubber Company, Nara, Japan.

The three-way valve 14 is a conventional valve used in the medical industry for controlling the flow of fluids to a patient. The valve has an inlet port 34, a sample outlet port 36 and a delivery outlet port 38. In one embodiment, the inlet and sample outlet ports are fitted with female receptacles and the delivery outlet port 38 has a male fitting.

The filter 16 has an outlet port 44 and inlet port 46 communicating with a filter element 45. In one embodiment, the outlet port 44 is a male fitting adapted to be received by the female receptacle of the inlet port 34 of the three-way valve 14. As is discussed in greater detail below, the inlet port 46 is fitted with a female receptacle which is adapted to receive the male outlet of the oxygen-containing gas reservoir assembly 18.

In a preferred embodiment, the oxygen-containing gas reservoir assembly 18 comprises an oxygen-containing gas reservoir tank 50 having, at one end, an inlet port 52 connected to a shut-off valve 54. An outlet port 56 is attached to the opposite end of the tank 50 and is connected to a T-union 58 by a short tube 59 in a gas-tight arrangement. A gas pressure gauge 60 and a shut-off valve 62 are both attached to the T-union. A connector 64 connects the valve 62 to the inlet port 46 of the filter 16.

In a preferred embodiment, the oxygen-containing gas supply assembly 20 comprises an oxygen-containing storage tank 68 connected to a conventional two-stage regulator 70. Gas supply tubing 74 is connected to the shut-off valve 54 of the inlet port of the gas reservoir assembly 18 and to a standard gas supply tube adapter 72 which is attached to the regulator 70. The distal end 72a of adapter 72 and the outlet port (not shown) of the shut-off valve 54 have conventional fittings for attaching the tubing 74 in a gas-tight relationship. There are many conventional fittings on the market available for this purpose, such as SWAGELOK brand fittings provided by Swagelock Company of Cleveland, Ohio.

In the illustrated embodiment, the oxygen-containing gas reservoir assembly 18 is attached to the filter by means of the connector 64. In turn, the filter 16 is attached to the three-way valve 14 by means of the male fitting and female receptacle of the outlet port 44 and inlet port 34 respectively. The delivery outlet port 38 of the three-way valve is attached to a hypodermic needle 80 (See FIG. 2) by means of the male fitting and the female receptacle of the delivery outlet port 38 and the hypodermic needle 80 respectively. The needle acts as a connector between the oxygenation system and the bag 12 and is adapted to be inserted through the rubber septum 31 (shown in FIG. 2) in the multi-purpose port 30 of the bag. The needle, when in place through the port 30 provides fluid communication between the three-way valve and the interior of the bag.

The perfluorocarbon emulsion formulation containment bags normally are supplied with 500 mL of the perfluorocarbon emulsion formulation.

In one embodiment, the perfluorocarbon emulsion formulation is supplied in a containment bag accompanied by two annex aqueous solutions. One of the annex solutions contains sodium chloride, potassium chloride and sodium bicarbonate. The other annex solution contains magnesium chloride and calcium chloride. These electrolytes are not formulated with the emulsion at the time of manufacture in order to prevent the inadvertent precipitation of magnesium and calcium carbonate solids. The perfluorocarbon emulsion in the bag contains non-ionic surfactants, phospholipids, a fatty acid or alkali metal salt thereof and a glycerol. This composition is vigorously mixed during manufacture to form a stable stem-emulsion which contains perfluorocarbon particles surrounded by phospholipids. Preferably, at least 90% of the particles by weight have a diameter of 0.2 microns or less. It has been found that the stem-emulsion is stable to freezing and freezing preserves the stem-emulsion. Accordingly, the stem-emulsion is normally supplied in the frozen form.

The bag containing the stem-emulsion is thawed before use. After thawing, the annex solution containing sodium chloride, potassium chloride and sodium bicarbonate is added to the stem-emulsion and is lightly agitated to ensure thorough mixing. Thereafter, the second annex solution comprising magnesium chloride and calcium chloride is added to the stem-emulsion to form the perfluorocarbon emulsion formulation. The perfluorocarbon emulsion formulation is not oxygenated when manufactured or when supplied to medical facilities because the plastic containment bag is permeable to gases, such as $O_2$. Thus, if the emulsion was oxygenated at the time of manufacture, oxygen would diffuse out of the bag before use, lowering the $pO_2$ of the emulsion formulation possibly to below a desired value, e.g., to below 600 mmHg. Thus, to ensure that the emulsion formulation will supply the patient or animal with an oxygen-enriched medium, the perfluorocarbon emulsion formulation is oxygenated shortly before use. Preferably, the emulsion formulation is oxygenated within 12 hours in advance of its actual use. In the preferred embodiment of the present invention, FLUOSOL®-DA 20%, brand of perfluorocarbon emulsion is utilized. FLUOSOL®-DA perfluorocarbon emulsion formulation is supplied by the Green Cross Corporation of Osaka, Japan. The formulation of FLUOSOL®-DA 20%, is as follows:

| Perfluorodecalin | 14.0 w/v % |
|---|---|
| Perfluorotri-n-propylamine | 6.0 w/v % |
| Pluronic F-68 | 2.7 w/v % |
| Yolk phospholipids | 0.4 w/v % |
| Potassium oleate | 0.04 w/v % |
| Glycerol | 0.8 w/v % |
| NaCl | 0.600 w/v % |
| KCl | 0.034 w/v % |
| $MgCl_2$ | 0.020 w/v % |
| $CaCl_2$ | 0.028 w/v % |
| $NaHCO_3$ | 0.210 w/v % |
| Glucose | 0.180 w/v % |

It has been found that aqueous emulsions of perfluorocarbons are not as readily and quickly oxygenated as "straight" perfluorocarbon compositions. It is believed that this is a result of the low oxygen solubility in the aqueous phase. The oxygen must first dissolve into the aqueous phase, the major phase and then diffuse into the perfluorocarbon particles. Oxygen has relatively low solubility in water—about 3 w/v% at 37° C.—whereas perfluorocarbons have relatively high solubility for oxygen—40 w/v% or more as 37° C. Thus, during oxygenation, it is believed that the oxygen dissolution in the aqueous phase is the rate limiting step for oxygenation. The oxygenation is hastened by oxygenating at an elevated pressure and with agitation. However, agitation must be moderate to prevent coalescence of the perfluorocarbon emulsion particles.

Ideally, the emulsion formulation is oxygenated to an oxygen partial pressure of at least about 600 mmHg, most preferably to at least about 720 mmHg. To oxygenate the emulsion formulation, the emulsion formulation must be supplied with sufficient oxygen at a sufficient pressure and with sufficient agitation to permit dissolution of the oxygen into the emulsion formulation.

OPERATION

Referring to FIG. 1, in practice of the present invention, the adapter 72 is attached to the two-stage regulator 70 of a medical oxygen tank 68. The gas shut-off valve 54 of the inlet port 52 of the sterile oxygen-containing gas reservoir 50 is connected to the sterile gas supply tube 74. The other end of the gas supply tube 74 is attached to the adapter 72 on the two-stage regulator. In one embodiment, medical oxygen (95% oxygen and 5% carbon dioxide) at about 80 pounds per square inch gage pressure (psig) is delivered to the oxygen containing gas reservoir 50 by opening the shut-off valve 54 at the inlet of tank 50 and closing the shut-off valve 62 at the outlet. When the gas pressure in the tank 50 is equal to the outlet gas pressure from the regulator, the shut-off valve 54 is closed. The oxygen-containing gas supply tube 74 is removed from the adaptor 72 and, optionally, from the shut-off valve 54.

A sterile 18-gauge hypodermic needle 80 (see FIG. 2) is inserted through the rubber septum 31 of the multipurpose port 30 of the perfluorocarbon emulsion containment bag 12. The delivery outlet port 38 of the three-way valve 14 is attached to the female receptacle of the hypodermic needle 80. The filter 16 is attached to the inlet port 34 of the three-way valve. During the operation of filling the bag 12 with oxygen-containing gas, the three-way valve is initially closed with respect to the delivery outlet port 38. The oxygen-containing gas reservoir 50 that has been charged with carbogen (the oxygen containing gas) is attached to the inlet port 46 of the filter 16. The three-way valve 14 is then manipulated to open the delivery outlet port 38, which closes the sample outlet port 36. The shut-off valve 62 is then opened to supply medical oxygen to the containment bag 12. When the pressures of the tank and the containment bag are equal, as shown by a constant reading on the gas pressure gauge 60, the three-way valve 40 is manipulated to close the delivery outlet port 38. The gas reservoir assembly 18 is then removed from the filter 16 and the filter, three-way valve 14 and the containment bag 12 are agitated for a period of at least 6 minutes to dissolve the oxygen in the perfluorocarbon emulsion formulation. By "agitation", it is meant that the bag 12 is moved sufficiently to impart a motion to the liquid in the bag. This motion or agitation can preferably be provided by means of an orbital shaker such as provided by Labline Company of Chicago, Ill., under the Trademark JUNIOR ORBIT SHAKER.

After the perfluorocarbon emulsion has been oxygenated to the desired partial pressure, which can be determined by sampling through the three-way valve or by time based on past experience, it is transferred to a large syringe for delivery to the patient. Transfer of the oxygenated perfluorocarbon emulsion formulation to the delivery syringe is made through the three-way valve sample outlet port 36. If desired, the bag can be vented through the three-way valve and filter either before or during the transfer process.

Since the perfluorocarbon emulsion formulation is normally intravenously injected into the patient, it is essential that the oxygenated emulsion formulation be sterile. Accordingly, the hypodermic needle 80, the three-way valve 40 and the filter 16, and other associated components must be sterilized before use in the oxygenation operation. The filter is added to the system as a sterilization safeguard. Preferably, the filter has a 0.2 micrometer filter element which will entrap all particles having a diameter greater than 0.2 micrometers. This filter will effectively remove any bacteria in the gas stream being supplied from the oxygen-containing gas reservoir 50 to the containment bag 12. In an alternative embodiment of the present invention, the filter is attached to the delivery outlet port of the three-way valve and the hypodermic needle 80 is attached to the outlet port of the filter.

The following examples are presented to further illustrate the practice of the present invention. These examples are not intended to limit the scope of the invention.

EXAMPLE 1

A MEDIDEX brand bag containing 500 mL of an aqueous emulsion of FLUOSOL®-DA, 20% was removed from its protective bubble packaging. The frozen MEDIDEX bag was placed into a polyethylene bag which was then sealed. The FLUOSOL®-DA emulsion formulation was thawed by immersing the bag in a water bath having a temperature no greater than 25° C. for approximately 30 minutes. At the same time, two annex solutions for the FLUOSOL®-DA, 20% emulsion were permitted to equilibrate to room temperature (21°-25° C.).

When the FLUOSOL®-DA, 20% was completely thawed, the MEDIDEX brand bag was removed from the water bath and the protective polyethylene bag was removed and discarded. A protective cap which had been in place over the multi-purpose port of the MEDIDEX bag was removed and the rubber septum of the multi-purpose port was swabbed with alcohol.

Protective caps on the annex solution bottles were removed and the rubber septum of each bottle was swabbed with alcohol to sterilize the septum. A vent needle was inserted in each of the annex solution bottles. 30 milliliters (mL) of annex solution "C" (a sterile aqueous solution containing NaCl, KCl and NaHCO$_3$) was withdrawn using a syringe with an 18-gauge needle inserted into the rubber septum of the annex solution "C" bottle; the needle was inserted next to the vent needle in a 50 mL syringe. The annex solution "C" bottle contains an excess of 30 mL of solution and some solution remained in the bottle after the 30 mL were withdrawn.

The 30 mL of annex solution "C" was injected into the FLUOSOL® bag through one of the puncture zones on the rubber septum of the multi-purpose port of the bag. The 18-gauge hypodermic needle, inserted through the rubber septum of the multi-purpose port of the bag was left in the rubber septum for the remainder of the operation. The 18-gauge needle was allowed to remain in the rubber septum to prevent bag contamination by repeated entries into the septum with a needle. After the addition of the annex solution "C", the contents of the bag were gently mixed.

Using a different 18-gauge hypodermic needle and a 50 mL syringe, 35 mL of annex solution "H" (a sterile aqueous solution contianing MgCl$_2$ and CaCl$_2$) was withdrawn from the annex solution "H" bottle by inserting the syringe needle through the bottle's septum. The 35 mL of annex solution "H" was injected into the FLUOSOL bag through the 18-gauge hypodermic needle already in place in the rubber septum of the bag. The contents of the bag, with the needle and syringe still attached to the bag, were lightly agitated to ensure thorough mixing. This step was repeated again with an additional 35 mL of annex solution "H". A total of 70 mL of annex solution "H" was added to the bag.

The 50 mL syringe was removed from the 18-gauge needle in the rubber septum of the multi-purpose port of the bag. A three-way stop cock having a male receptacle was attached to the 18-gauge needle. A 0.2 micrometer filter having a male fitting was attached to the female receptacle of the inlet port of the three-way stop cock. During this operation, the "off" arrow on the stop cock was pointing towards the outlet of the stop cock attached to the 18-gauge needle in the rubber septum of the multi-purpose port of the FLUOSOL® bag to prevent the escape of any contents of the bag.

The used syringes, hypodermic needles and annex solution bottles were discarded in an appropriate manner.

A one-quarter inch SWAGELOK brand union was attached to a medical oxygen tank adapter mounted on a medical oxygen tank regulator. The union was tightened and checked for gas leaks. The equipment illustrated in FIG. 1 was assembled. The shut-off valve 62 was closed. The shut-off valve 54 was opened to permit gas from the medical gas tank to flow into the tank 50 which had a 75 mL capacity. The medical oxygen cylinder tank was turned on and pressure was allowed to increase until the gas pressure gauge 60 indicated a pressure of 80 psig, then shut-off valve 54 was closed. The medical oxygen tank was then turned off. At this point, the oxygenation system was disconnected by unscrewing the fitting 72a at the outer end of adapter 72. Alternatively the tube 74 can be removed from the valve 54. The gas reservoir assembly 18 was connected to the filter 16.

After the equipment was assembled as described above the three-way stop cock 14 was manipulated so that the arrow on the handle pointed towards the middle sampling port to open the flow path between the oxygen-containing gas reservoir tank 50 and the bag 12. The oxygen-containing gas reservoir tank contained 75 mL of medical oxygen at 80 psig. Accordingly, the oxygenation system from the 18-gauge needle in the rubber septum of the multi-purpose port of the bag to the oxygen-containing gas reservoir was held firmly while releasing the gas into the bag. The shut-off valve 62 was opened and gas from the tank 50 was delivered rapidly into the bag 12. The valve 62 was closed when the pressure stopped dropping as measured on the gauge 60. This pressure was about 3 psig. Preferably the pressure of the gas introduced into the bag is greater than about 1 psig. The bag, now filled with gas, was distended. The handle on the three-way stop cock 14 was turned counterclockwise so that the "off" arrow pointed toward the bag, thereby sealing the outlet 38 from the outlet 36 and the inlet 34. The oxygen-containing gas reservoir assembly 18 was then removed from the filter 16 at the connection 64.

The inflated bag 12, with a needle 80, stop cock 14 and filter 16 attached, was placed on an orbital shaker supplied by Labline Company of Chicago, Ill. under the trade name JUNIOR ORBIT SHAKER and agitated for 6 minutes at 100 rpm. The FLUOSOL®-DA emulsion formulation in the bag was sampled from time to time through the three-way stop cock (middle port 36) by turning the handle of the valve 14 180° in a counter clockwise direction to determine the pO$_2$ of the emulsion formulation. Agitation was continued at 1 to 2 minute intervals with sampling until the pO$_2$ of the FLUOSOL® emulsion formulation was 600 mmHg or greater. A pO$_2$ of 600 or more mmHg was found to hold stable for two hours.

EXAMPLE 2

Four MEDIDEX brand bags containing 500 mL of FLUOSOL®-DA, 20% emulsion formulation were oxygenated according to the procedure set forth in Example 1. The FLUOSOL® in Bags 1, 2 and 3 was oxygenated with a gas supplied from a reservoir tank having a capacity of 40 mL which was charged with medical oxygen to a pressure of 115 psig. The FLUOSOL®-DA in Bag 4 was oxygenated with a gas supplied from a reservoir tank having a capacity of 75 mL which was charged with medical oxygen to a pressure of 80 psig.

The FLUOSOL®-DA Bag 1 was oxygenated without agitation and samples were drawn every 7 minutes to determine the $pO_2$ of the FLUOSOL®-DA emulsion formulation. The bag was then agitated at 24 hours and a sample was taken following the agitation. Bag 2 was agitated during oxygenation of the FLUOSOL®-DA only briefly by hand before sampling. Samples of FLUOSOL®-DA were drawn every two minutes to determine the $pO_2$ of the FLUOSOL®-DA sample. The bag was then agitated at 22 hours and a sample was taken following the agitation. Bag 3 was agitated continuously during oxygenation of FLUOSOL®-DA using a JUNIOR ORBIT SHAKER provided by Labline Company of Chicago, Ill. at 100 rpm. Samples were drawn every two minutes to determine the $pO_2$ of the FLUOSOL®-DA emulsion formulation. In Bag 4, the FLUOSOL®-DA emulsion formulation was oxygenated with constant agitation. Samples were drawn every two minutes to determine the $pO_2$ of the FLUOSOL®-DA emulsion formulation. The bag was then removed from the agitation unit and samples were drawn at 30 minutes, 90 minutes, 210 minutes and at 22 hours to determine the $pO_2$ of the emulsion formulation.

Figure 3:
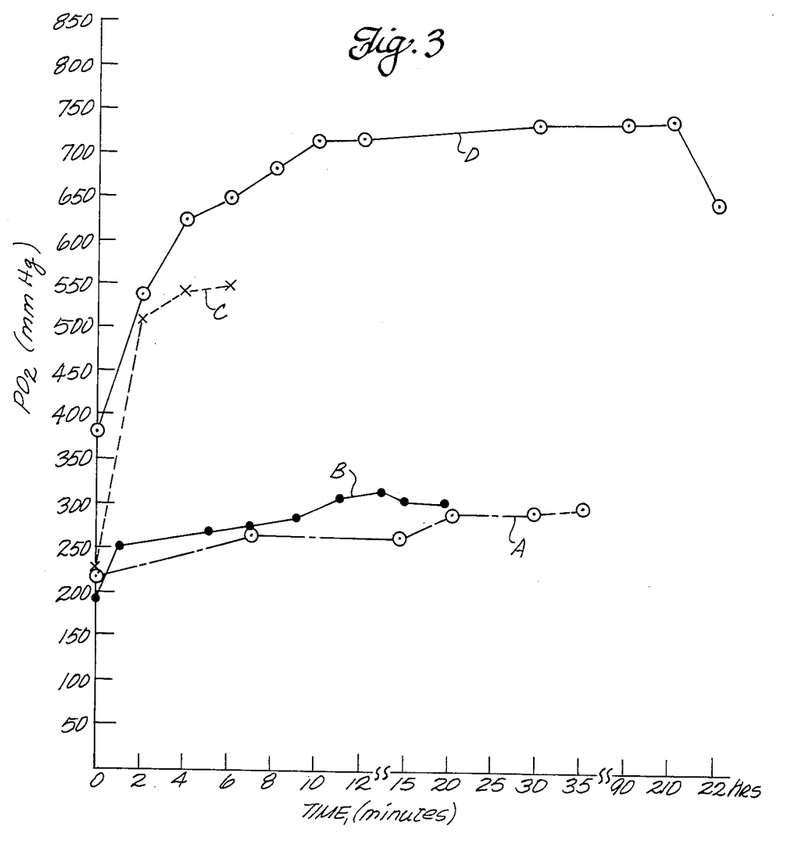
FIG. 3 is a graph illustrating the partial pressure of oxygen in the perfluorocarbon emulsion formulation during oxygenation, employing no agitation, some agitation and continuous agitation for given volumes of oxygen-containing gas delivered to the emulsion formulation.

The results of the experiments of Example 2 are set forth in FIG. 3. Graphs A, B, C and D of FIG. 3 show the $pO_2$ of the FLUOSOL®-DA emulsion formulation in Bags 1, 2, 3 and 4 respectively as a function of time.

Graphs A and B show that FLUOSOL®-DA is not oxygenated to the desired $pO_2$ value of greater than about 600 mmHg if the bag containing the FLUOSOL DA is not agitated in accordance with practice of this invention. Graph C, while showing that when agitation is used the $pO_2$ increases rapidly, also shows that when medical oxygen at 115 psig from a 40 mL container is provided it is not sufficient to raise the $pO_2$ of FLUOSOL®-DA to over 600 mmHg. Graph D on the other hand, shows that it takes only about 6 minutes to oxygenate FLUOSOL®-DA to a $pO_2$ of greater than about 600 mmHg when a 75 mL volume of medical oxygen is used at 80 psig and the bag containing the FLUOSOL®-DA and oxygen is agitated in accordance with practice and principles of this invention. Graph D further shows that the oxygenated emulsion formulation loses oxygen between 3.5 and 22 hours after the oxygenation of FLUOSOL®-DA. This loss, as is set forth above, is likely due to diffusion of $O_2$ through the plastic bag. Although it is not shown on the graphs, when Bag 1 was agitated at 24 hours and a sample was taken the $pO_2$ was 488 mmHg. The sample taken from Bag 2, after agitation at 22 hours, showed a $pO_2$ of 480.6 mmHg.

EXAMPLE 3

Figure 4:
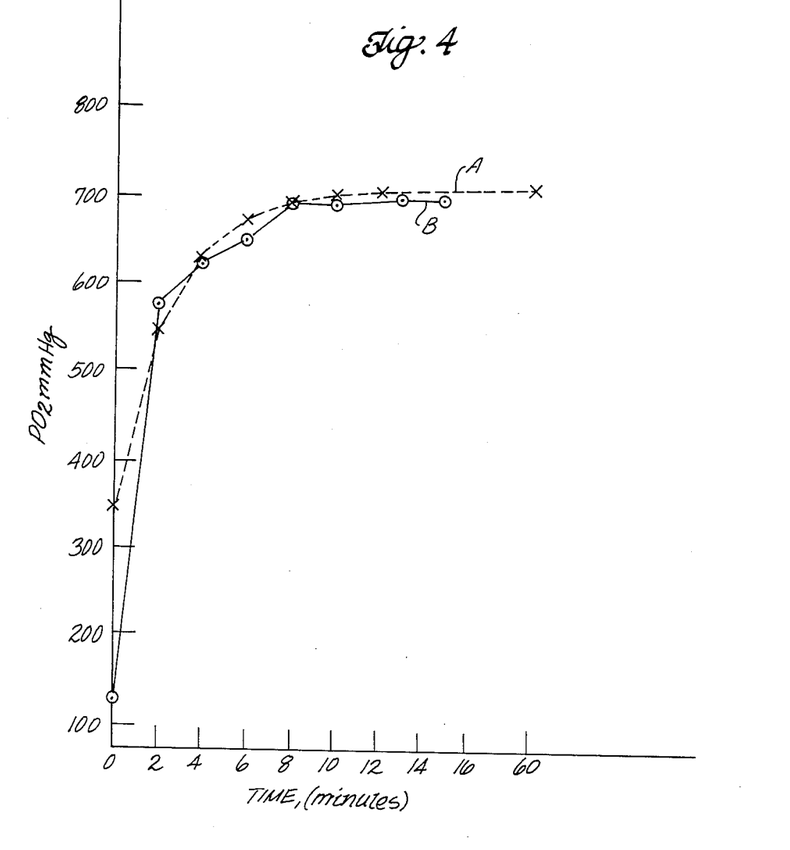
FIG. 4 is a graph showing the partial pressure of oxygen in a perfluorocarbon emulsion formulation during oxygenation.

Two MEDIDEX brand bags containing FLUOSOL®-DA, 20% emulsion were oxygenated in accordance with the procedure of Example 1 employing an oxygen-containing gas reservoir tank having a capacity of 75 mL. The tank was charged with medical grade oxygen at 80 psig. Each bag was agitated continuously for 12 minutes on a JUNIOR ORBITAL SHAKER. The first bag was sampled at two minute intervals up to 12 minutes and then finally sampled at the end of 60 minutes. The second bag was sampled at 2 minute intervals up to 10 minutes and then sampled at 13 minutes and 15 minutes. The reproducibility of the method was demonstrated and graphically shown in FIG. 4 where the $pO_2$ of the FLUOSOL® emulsion formulation for the first and second bags are illustrated in Graphs A and B, respectively.

EXAMPLE 4

The procedure of Example 1 was repeated twice employing an oxygen-containing gas reservoir tank having a capacity of 75 mL in order to determine the partial pressure of $CO_2$ ($pCO_2$), as well as the $pO_2$ of the FLUOSOL® emulsion formulation during the oxygenation. The test results are set forth below:

| Sampling Time | TEST 1 | |
|---|---|---|
| | $pCO_2$ (mmHg) | $pO_2$ (mmHg) |
| 0 mins. | 50.0 | 346.1 |
| 2 mins. | 45.0 | 552.5 |
| 4 mins. | 48.4 | 630.8 |
| 6 mins. | 48.8 | 678.3 |
| 8 mins. | 51.3 | 701.0 |
| 10 mins. | 40.8 | 704.8 |
| 12 mins. | 55.0 | 708.9 |
| 60 mins. | 44.7 | 716.1 |

| Sampling Time | TEST 2 | |
|---|---|---|
| | $pCO_2$ | $pO_2$ |
| 0 mins. | 66.9 | 377.5 |
| 2 mins. | 65.4 | 535.3 |
| 4 mins. | 52.7 | 623.5 |
| 6 mins. | 62.5 | 645.5 |
| 8 mins. | 57.1 | 676.5 |
| 10 mins. | 54.0 | 715.7 |
| 12 mins. | 62.9 | 716.3 |
| 30 mins.* | 64.1 | 730.7 |
| 90 mins.* | 62.0 | 738.4 |
| 210 mins.* | 60.0 | 730.0 |

*The 30 minute, 90 minute and 210 minute samples were not agitated.

The results of Example 4 show that carbon dioxide is more rapidly dissolved in the FLUOSOL®-DA emulsion formulation than is oxygen.

In another preferred embodiment of the practice of the present invention, the oxygen-containing gas is supplied to the bag 12 containing the perfluorocarbon emulsion formulation from a precharged disposable gas cartridge. This embodiment can be understood by turning to FIG. 5, in addition to FIGS. 1 and 2.

Figure 2:
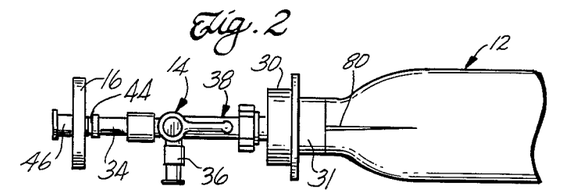
FIG. 2 is a semi-schematic fragmentary elevational view of a portion of the oxygenation system shown in FIG. 1.

In this embodiment, all of the equipment upstream from the filter 16, as shown in FIG. 1, is eliminated, while the remaining components are arranged as shown in FIG. 2. Thus, the needle 80 is through the septum 31 of the port 30 of the perfluorocarbon emulsion containment bag 12. The three-way valve 14 is connected to the needle and the filter 16 is on the three-way valve. A gas cartridge 82 (shown in FIG. 5) is connected by means of a connector 84 to the inlet port 46 of the filter 16.

Figure 5:
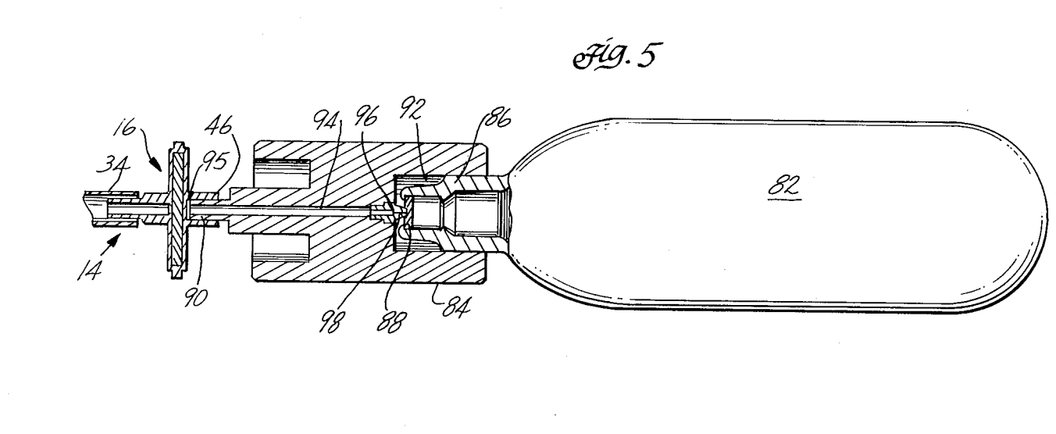
FIG. 5 is a semi-schematic fragmentary elevational view in partial cross-section of a portion of another embodiment of an oxygenation system provided in accordance with practice of principles of the present invention.

The cartridge 82 of one embodiment is made of stainless steel and includes a neck portion 86, which is closed at its mouth by a lead seal 88. The connector 84 can be made of various metals, such as brass, or it can be made of a plastic. The connector includes a male fitting 90 at one end for insertion into the inlet port 46 of the filter 16. A hollow cavity 92 at the end of the connector opposite the fitting 90, is sized to receive the neck portion 86 of the cartridge. A conduit or passage 94 extends from an outlet 95 at the male fitting 90 through the center of the connector 84. A pointed metal tip 96 is mounted at the end of the passage 94 opposite from the outlet 95. The tip has a passage 98 through its center which connects with the connector passage 94. The tip is designed to pierce the lead seal 88 when the connector is mounted on the cartridge.

To operate the system of this embodiment, the components are arranged as is shown in FIG. 2. The male fitting 90 of the connector 84 is inserted into the inlet port 46 of the filter 16. At this time, the three-way valve 14 may be either in the open or closed position, as desired. After the connector is mounted on the filter, the neck 86 of the cartridge 82 is inserted into the cavity 92 so that the lead seal 88 is aligned with the pointed tip 96. Sufficient force is then applied to the cartridge along its longitudinal axis so that the tip 96 pierces the lead seal enabling the gas in the cartridge to pass through the passage 98 in the tip, through the connector passage 94, and thence, through the filter 16, the three-way valve 14 and into the bag 12. If the three-way valve is closed at the time the point pierces the lead seal, the three-way valve can be opened when it is desired to supply the gas from the cartridge into the bag.

In one embodiment, the cartridge has a 95 ml capacity and is provided with carbogen (95% $O_2$, 5% $CO_2$) at a pressure of 65 psig. A cartridge of this size containing carbogen at 65 psig provides sufficient oxygen so that the $pO_2$ in the 500 ml emulsion formulation at the completion of the oxygenation step is at least about 720 mmHg. If desired, however, cartridges having other sizes with carbogen at other pressures can be used. Furthermore, if desired, the oxygen-containing gas can comprise 97% $O_2$ and 3% $CO_2$ or other combinations, as desired.

In yet another preferred embodiment of practice of the present invention, the oxygen containing gas may be supplied to the bag containing the perfluorocarbon emulsion formulation without using a gas reservoir, such as the reservoir 50. In this embodiment, the system can be connected as shown in FIGS. 1 and 2 except that the reservoir tank 50 is deleted. The valves can be manipulated so that oxygen containing gas is transferred directly from the tank 68 into the bag 12 until the pressure in the bag, as read on the gauge 60, is at about 3 psig. The valves from the tank 68 are then shut. This procedure can take about 10 seconds. If desired the bag can be supplied with the oxygen containing gas in more or fewer than 10 seconds. After the 3 psig pressure is reached, the bag is removed and agitated as described above.

The above descriptions of preferred embodiments of methods and devices provided in accordance with practice of principles of the present invention are for illustrative purposes. Because of variations which will be apparent to those skilled in the art, the present invention is not intended to be limited to the particular embodiments described above. The scope of the invention is defined in the following claims.

What is claimed is:

1. A method for oxygenating a perfluorocarbon emulsion formulation comprising the steps of:
   (a) placing a perfluorocarbon emulsion formulation in a closed container;
   (b) introducing an oxygen-containing gas from a separate container into the closed container; and
   (c) agitating the closed container for a time sufficient to dissolve such oxygen in the perfluorocarbon emulsion formulation so that the oxygen in the oxygen-containing gas above the emulsion formulation approaches equilibrium with the oxygen dissolved in the perfluorocarbon emulsion formulation.

2. The method according to claim 1 wherein the oxygen-containing gas comprises about 95% by volume oxygen and about 5% by volume carbon dioxide.

3. The method according to claim 1 wherein a sufficient amount of oxygen-containing gas is introduced into the closed container so that the partial pressure of oxygen in the perfluorocarbon emulsion formulation is at least about 600 mm Hg at the time agitation of the closed container is completed.

4. The method according to claim 1 wherein the oxygen-containing gas is provided at a sufficient pressure and agitation and in an amount sufficient so that the partial pressure of oxygen in the perfluorocarbon emulsion formulation is at least about 720 mm Hg at the time agitation of the closed container is completed.

5. The method according to claim 1 wherein the oxygen containing gas is introduced into the closed container to provide a pressure in excess of 1 psig.

6. The method according to claim 1 wherein the closed container is a flexible, water impermeable bag.

7. A method for oxygenating a perflurocarbon emulsion formulation comprising the steps of:
   (a) providing a perfluorocarbon emulsion formulation comprising a mixture of perfluorodecalin and perfluorotri-n-propylamine in a closed container;
   (b) introducing a selected amount of an oxygen-containing gas into the closed container; and
   (c) shaking the closed container for a selected time to thereby agitate the perfluorocarbon emulsion and to dissolve oxygen in the perfluorocarbon emulsion, the combination of the selected amount of oxygen-containing gas and the selected time being such that at the time shaking of the container is completed the partial pressure of oxygen in the perfluorocarbon emulsion is at least 600 mmHg.

8. The method according to claim 7 wherein the combination of the selected amount of oxygen-containing gas and the selected time is such that at the time shaking of the container is completed the partial pressure of oxygen in the perfluorocarbon emulsion is at least 720 mmHg.

9. The method according to claim 7 wherein the oxygen-containing gas comprises about 95% by volume oxygen and about 5% by volume carbon dioxide.

10. The method according to claim 7 wherein the oxygen containing gas is introduced into the closed container to provide a pressure of approximately 3 psig.

11. The method according to claim 7 wherein the closed container is a flexible, water impermeable bag.

* * * * *